(12) United States Patent
Hausmann et al.

(10) Patent No.: US 7,984,714 B2
(45) Date of Patent: Jul. 26, 2011

(54) MANAGING OBSTRUCTIVE SLEEP APNEA AND/OR SNORING USING LOCAL TIME RELEASED AGENTS

(75) Inventors: Gilbert Hausmann, Felton, CA (US); Shannon Eleanor Campbell, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 703 days.

(21) Appl. No.: 11/537,176

(22) Filed: Sep. 29, 2006

(65) Prior Publication Data

US 2008/0082041 A1    Apr. 3, 2008

(51) Int. Cl.
*A61F 5/56*    (2006.01)
*A61F 2/00*    (2006.01)
*A61F 13/00*    (2006.01)
*A61C 5/14*    (2006.01)

(52) U.S. Cl. ......... 128/848; 128/859; 424/426; 424/434

(58) Field of Classification Search .................. 128/848, 128/859; 602/902; 424/434, 435, 422, 423, 424/426; 514/237.5; 530/389.2
See application file for complete search history.

(56) References Cited

U.S. PATENT DOCUMENTS

| 5,502,067 | A  | * | 3/1996 | Morgan | 514/397 |
|---|---|---|---|---|---|
| 5,804,211 | A | * | 9/1998 | Robertson et al. | 424/434 |
| 6,034,117 | A | * | 3/2000 | Hedner et al. | 514/411 |
| 6,440,391 | B1 | * | 8/2002 | Jacob | 424/43 |
| 7,363,076 | B2 | * | 4/2008 | Yun et al. | 607/3 |
| 2003/0149445 | A1 | | 8/2003 | Knudson et al. | |
| 2005/0038013 | A1 | | 2/2005 | Gold | |
| 2005/0048086 | A1 | * | 3/2005 | Flashner-Barak et al. | 424/400 |
| 2007/0292524 | A1 | * | 12/2007 | Ringe et al. | 424/497 |

FOREIGN PATENT DOCUMENTS

| WO | 97/22339 | 6/1997 |
|---|---|---|
| WO | 2004/034963 | 4/2004 |
| WO | 2005/016327 A | 2/2005 |

OTHER PUBLICATIONS

International Search Report and Written Opinion, Mar. 10, 2008, 14 pages, PCT/US2007/079720.
A Short Practical Guide to Psychotropic Medications for Dementia Patents, Pharmacological Treatment of Alzheimer's Disease; Alabama's Alzheimer's Resource; http://www.alzbrain.org/quicklinks/practguide/AlzheimerTreatment.htm.

* cited by examiner

*Primary Examiner* — Patricia M Bianco
*Assistant Examiner* — Ophelia Hawthorne

(57) ABSTRACT

A method for managing at least one breathing condition may include storing an agent near a patient's airway and delivering the agent to the mucosal tissue in the pharyngeal area in a time-released manner during a sleep period. The delivered agent may cause increased contraction of muscle tissue in the pharyngeal area.

25 Claims, 6 Drawing Sheets

MANAGING OBSTRUCTIVE SLEEP APNEA AND/OR SNORING USING LOCAL TIME RELEASED AGENTS

TECHNICAL FIELD

The present disclosure relates generally to the field of breathing assistance systems, e.g., managing obstructive sleep apnea and/or snoring using local time released agents.

BACKGROUND

Obstructive Sleep Apnea (OSA) is a disorder in which the sufferer is unable to maintain patency of the upper airway while sleeping. The cause is typically a decrease in muscle tone in the tissues of the throat, although the condition can also be triggered or aggravated by being overweight. Symptoms of OSA may include impaired ability to concentrate during waking hours, memory loss, narcolepsy and, if untreated for a long period of time, heart disease emanating from repetitive, transient hypoxias and increased pulmonary vascular resistance. Snoring is often an indicator of OSA.

In recent years, continuous positive airway pressure (CPAP) therapy has become a common prescription for individuals suffering from OSA, snoring, and/or other breathing ailments. Such therapy may involve placement of a nose, mouth, or face mask on the patient during sleeping, while positive pressure air is continuously delivered to the patient through the mask. The positive pressure air may be delivered to the patient's upper airway to prevent the upper airway tissues from collapsing during sleep, thus reducing the occurrence and/or severity of OSA.

SUMMARY

According to one embodiment of the present disclosure, a method for managing at least one breathing condition may include storing an agent near a patient's airway and delivering the agent to the mucosal tissue in the pharyngeal area in a time-released manner during a sleep period. The delivered agent may cause increased contraction of muscle tissue in the pharyngeal area.

According to another embodiment of the present disclosure, a system for managing at least one breathing condition may include an agent delivery device and a time-release mechanism. The agent delivery device may be operable to deliver an agent to the mucosal tissue in the pharyngeal area, the agent operable to cause increased contraction of muscle tissue in the pharyngeal area. The time-release mechanism may be operable to control the delivery of the agent to the mucosal tissue in the pharyngeal area during a sleep period to cause increased contraction of muscle tissue in the pharyngeal area during the sleep period.

According to another embodiment of the present disclosure, a system for managing at least one breathing condition may include means for storing an agent near a patient's airway, and means for delivering the agent to the mucosal tissue in the pharyngeal area in a time-released manner during a sleep period. The delivered agent may cause increased contraction of muscle tissue in the pharyngeal area.

According to another embodiment of the present disclosure, an agent charging system for managing at least one breathing condition may include a reservoir of agent capable of supplying agent to an agent delivery system for delivering the agent to the mucosal tissue in the pharyngeal area. The agent may be operable to cause increased contraction of muscle tissue in the pharyngeal area.

BRIEF DESCRIPTION OF THE DRAWINGS

Some embodiments of the disclosure may be understood by referring, in part, to the following description and the accompanying drawings, in which like reference numbers refer to the same or like parts and, wherein.

DETAILED DESCRIPTION OF THE DRAWING

Selected embodiments of the disclosure may be understood by reference, in part, to FIGS. 1-6, wherein like numbers refer to same and like parts. The present disclosure relates generally to the field of breathing assistance systems, e.g., a method and apparatus for time releasing an agent locally in the pharyngeal area in order to control sleep apnea and/or snoring.

Figure 1:
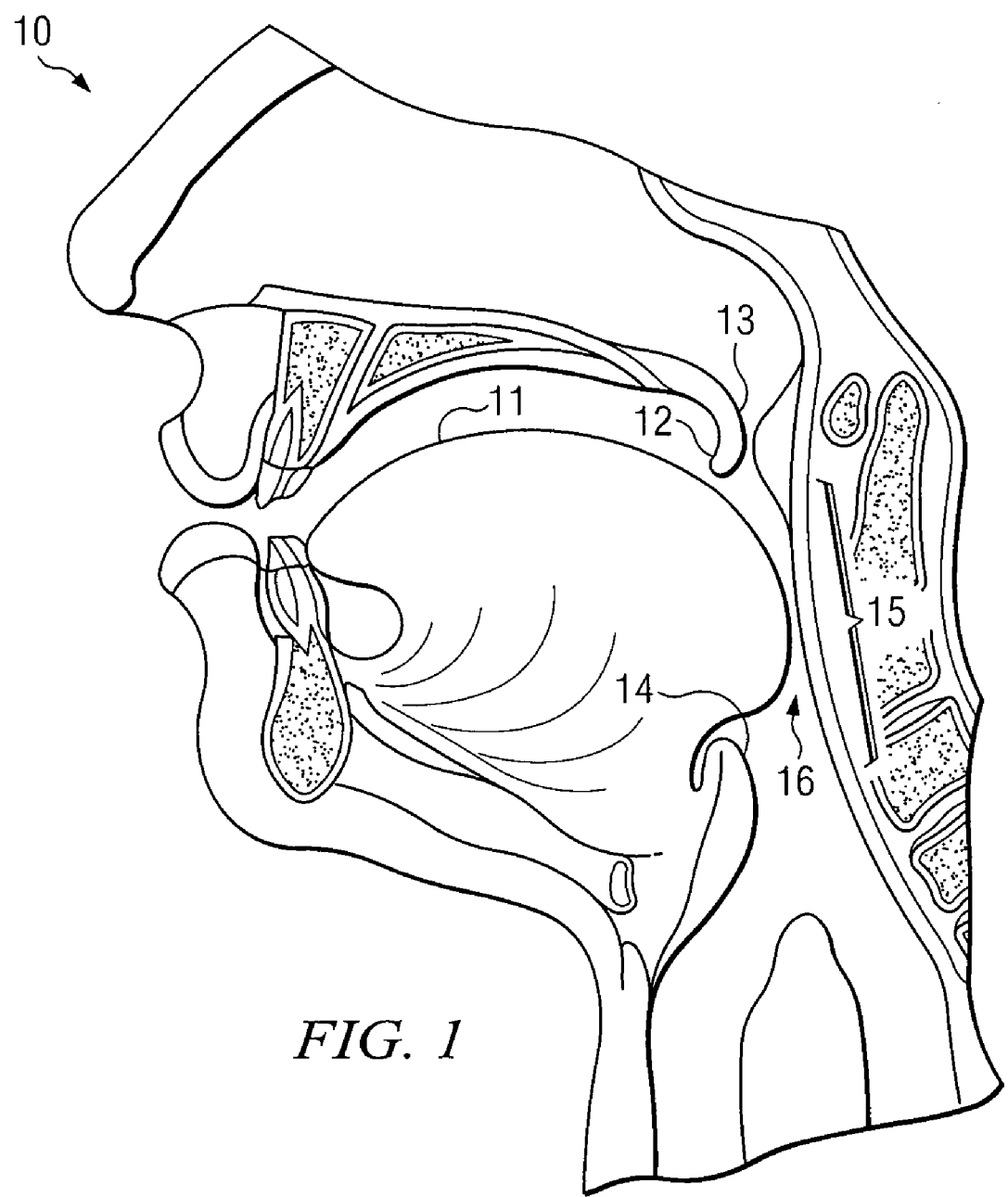
FIG. 1 illustrates a cross-sectional side view of a sleeping patient having a pharyngeal condition conducive to obstructive sleep apnea and/or snoring.

As shown in FIG. 1, a pharyngeal condition conducive to obstructive sleep apnea syndrome and/or snoring may exist when the tongue relaxes. FIG. 1 illustrates patient 10 in a sleeping state. When relaxed, tongue 11 may fall back onto uvula 12, epiglottis 14, and/or oropharynx 15 to restrict airway opening 16. The uvula 12 is located at the end of soft palate 13.

The term "patient" may refer to any person or animal that may receive assistance from any system disclosed herein, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, persons administering treatments or therapies for themselves, etc.

Certain embodiments of the present disclosure enhance the response of muscles to natural stimulation to improve muscle tone of the pharyngeal area, which may control at least one breathing condition. The term "breathing condition" may refer to obstructive sleep apnea, snoring, other full or partial blockages of the airway, or any other undesirable breathing condition.

Electrical impulses traveling through the nerve to the nerve ending (synaptic terminal) stimulate the release of acetylcholine, which crosses the synaptic cleft and binds to cholinergic receptors on the adjacent muscle cell membrane (motor end plate). This results in the opening of calcium ion channels in the muscle cell and stimulates that muscle cell to contract (excitation-contraction coupling). Improved muscle tone can be achieved either by increasing the amount of acetylcholine stimulating the muscle cells, or by stimulating the cholinergic receptor with another agent (cholinergic receptor agonist).

Acetylcholine is a small organic molecule that is released at certain (cholinergic) nerve ending as a neurotransmitter, wherein it may be excitatory or inhibitory. It is important in the stimulation of muscle tissue for muscle contraction. Acetylcholine functions to pass on a nerve impulse from one nerve cell to another nerve or muscle cell across a synapse. The transmission of an electrical impulse to the end of the nerve results in the release of acetylcholine neurotransmitter molecules into the synaptic cleft. When acetylcholine binds to the acetylcholine receptors on the striated muscle cell it opens channels in the muscle membrane. Calcium ions then enter the muscle cells and a muscle contraction results. The acetylcholine molecules in the synaptic cleft are quickly broken down into acetate and choline, which are taken up by the nerve cell to be recycled into acetylcholine again.

Certain embodiments of the present disclosure include systems or methods for causing increased contraction of muscle tissue in the pharyngeal area, which may eliminate or reduce a pharyngeal condition conducive to obstructive sleep apnea and/or snoring.

For example, to provide such increased contraction of muscle tissue in the pharyngeal area, an agent may be delivered to the mucosal tissue in the pharyngeal area (e.g., in a time-released manner or otherwise). Various types of agents may be used to (a) provide elevated levels of acetylcholine in the pharyngeal area (e.g., at neuromuscular junctions associated with the muscle tissue in the pharyngeal area), and/or (b) activate nicotinic receptors to cause the contraction of muscle tissue in the pharyngeal area. For example, certain agents may be used to increase the local concentration of acetylcholine in the pharyngeal area. Such agents may include acetylcholine and other suitable agents. As another example, certain agents may be used to prevent or slow the rate of degradation of acetylcholine in the pharyngeal area. Such agents may include cholinesterase inhibitors, other agents that slow or inhibit the enzyme acetylcholinesterase (which degrades the acetylcholine molecule), or other suitable agents. As another example, certain non-acetylcholine agents may be used to activate nicotinic (or cholinergic or acetylcholine) receptors to cause the contraction of muscle tissue in the pharyngeal area. Such nicotinic receptor agonists may include bethanechol, carbachol, cevimeline, pilocarpine, suberycholine, ambenoomium, donepezil, edrophonium, galantamine, neostigmine, physostigmine, pyridostigmine, rivastigmine, tacrine, or any other suitable agents.

Thus, as used herein, the term "agent" may refer to any one or more chemicals, compounds, medications, or other substances, in any form, that may be used to cause increased contraction of muscle tissue. Example agents may include acetylcholine, agents that slow or inhibit the enzyme acetylcholinesterase, cholinesterase inhibitors, bethanechol, carbachol, cevimeline, pilocarpine, suberycholine, ambenoomium, donepezil, edrophonium, galantamine, neostigmine, physostigmine, pyridostigmine, rivastigmine, tacrine, other nicotinic receptor agonists, or any other suitable agents.

As another example for providing increased contraction of muscle tissue in the pharyngeal area, neurons may be stimulated or activated to produce an increased amount of acetylcholine. As another example for providing increased contraction of muscle tissue in the pharyngeal area, cholinergic receptors may be directly stimulated.

Some embodiments may include systems or methods for delivering an agent in a time-released manner. For example, systems or methods may be provided for releasing an agent only during a period of intended rest (e.g., an 8 hour period), or portions of such rest period, thus avoiding over-stimulation (excessive muscle contractions) during active periods. According to some embodiments, a delivery system may comprise micro- or nano-spheres containing an agent, which spheres may be surface activated to adhere to the mucosal tissue of the pharyngeal area. Mucosa is moist tissue that lines particular organs and body cavities throughout the body, including the nose, mouth, lungs, and gastrointestinal tract. Glands along the mucosa secrete mucus (a thick fluid). In some embodiments, these spheres may be suspended in a spray or liquid solution (e.g., mouthwash). According to some embodiments, a delivery system may include one or more mucosal patches, which may release an agent in any suitable form. Other embodiments include delivery systems including small reservoirs and pumps to deliver an agent as desired.

Figure 2:
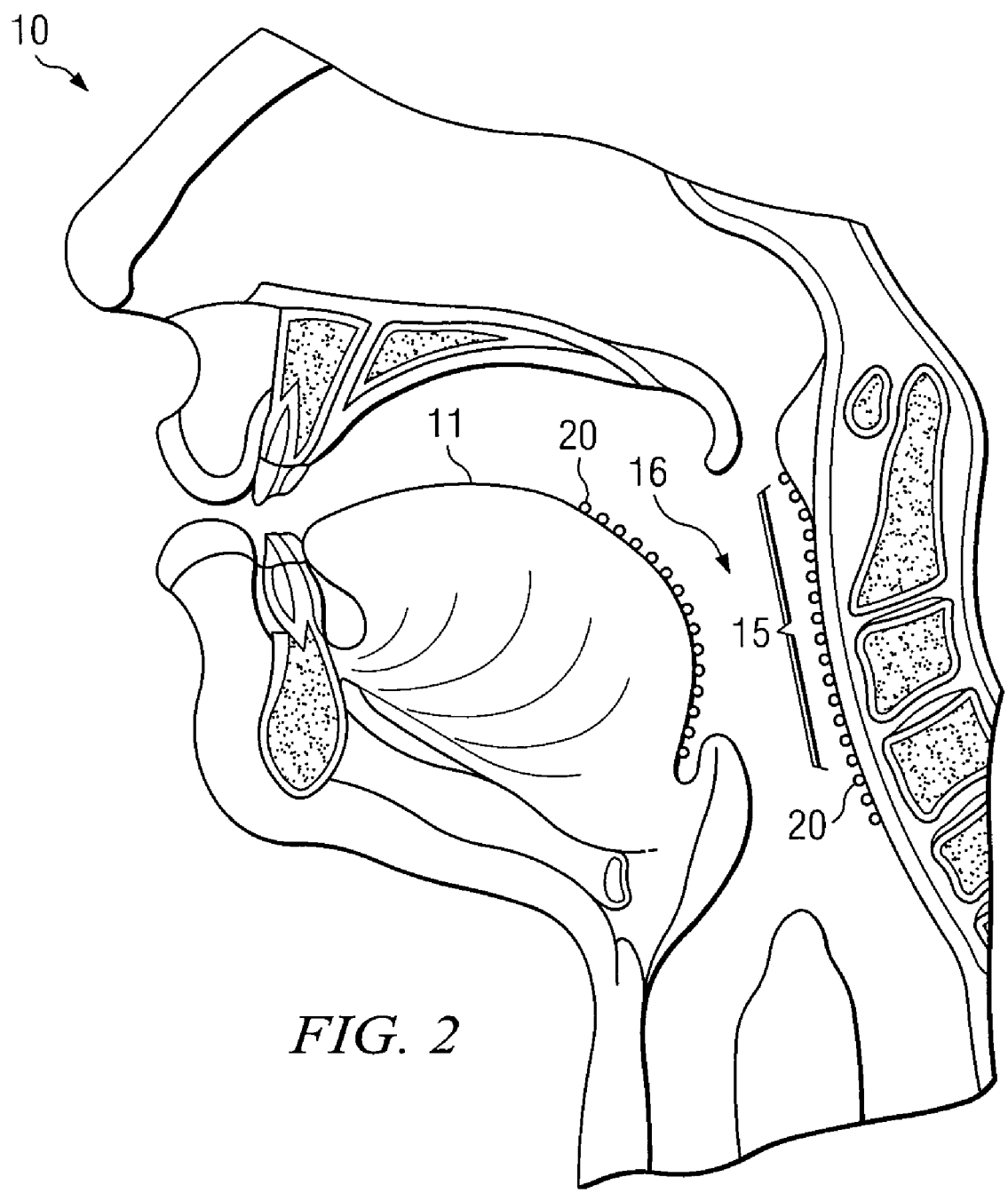
FIG. 2 illustrates a cross-sectional side view of one embodiment of a system for managing at least one breathing condition.

FIG. 2 illustrates a cross-sectional side view of patient 10 and an example system for managing at least one breathing condition, according to one embodiment of the disclosure. Patient 10 may be given a dose of acetylcholine through a nano-spheres delivery system, e.g., prior to the patient falling sleep. For purposes of this disclosure, the term "nano-spheres" is used to identify all types of nano-spheres, microbubbles, etc. known to persons of skill. Nano-spheres 20 may be delivered to the mucosal tissue of tongue 11 and/or the oropharynx 15. Nano-spheres 20 may include acetylcholine encapsulated in a membrane or other outer coating. As the membrane or coating dissolves, the acetylcholine is released to the mucosal tissue.

In some embodiments, a dose of nano-spheres 20 may include spheres 20 having membranes that dissolve at different rates. Thus, the dose may have a "time release" function such that acetylcholine may be delivered to the patient's tongue and/or oropharynx somewhat or substantially uniformly over the course of a sleeping period (e.g., an 8 hour period). For example, a dose may include nano-spheres 20 having membranes that dissolve at 1-hour, 2-hour, . . . , and 7-hour intervals such that fresh supplies of acetylcholine are released to the mucosal tissues throughout an 8 hour sleeping period. As illustrated in FIG. 2, the delivery of acetylcholine to the mucosal tissues of the pharyngeal area causes the muscles to contract to expand airway opening 16 (compare with FIG. 1), thus reducing or eliminating apnea events and/or snoring.

Acetylcholine-filled nano-spheres 20 may be delivered to the pharyngeal area through any deliver system known to persons of skill in the art. For example, the delivery system may include an aerosol that is administered orally, a spray that is administered orally, a liquid "mouthwash," a lozenge, etc.

Figure 3:
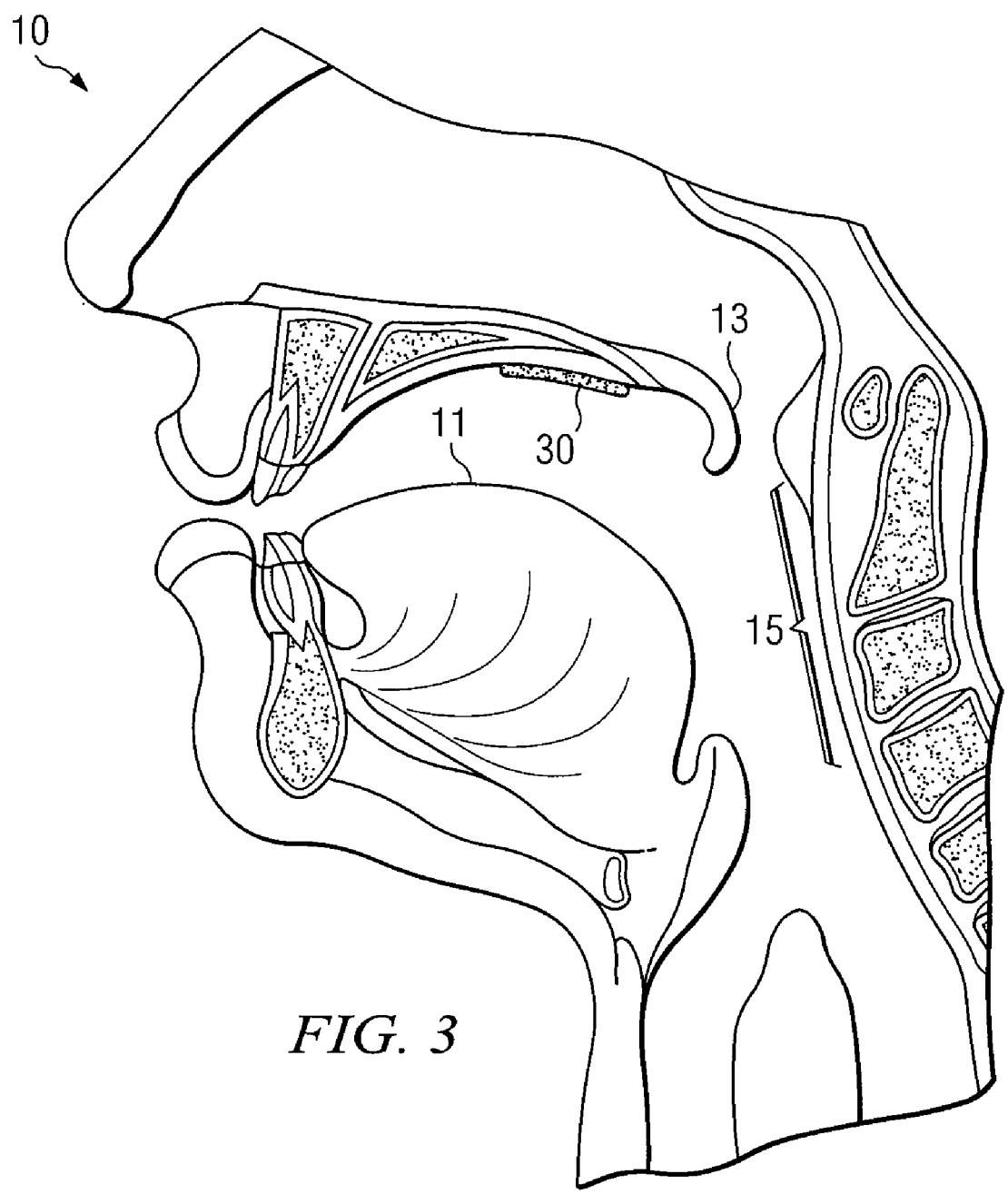
FIG. 3 illustrates another cross-sectional side view of one embodiment of a system for managing at least one breathing condition.

FIG. 3 illustrates a cross-sectional side view of patient 10 and another example system for managing at least one breathing condition, according to one embodiment of the disclosure. In this embodiment, patient 10 may be given a dose of acetylcholine through a mucosal patch delivery system, e.g., prior to patient 10 falling sleep. Mucosal patch 30 may be adhered to the underside of soft palate 13 in order to deliver acetylcholine to the mucosal tissue of the pharyngeal area, e.g., tongue 11 and/or oropharynx 15. Mucosal patch 30 may be a dissolving film that sticks to oral mucosa. Mucosal patch 30 may be a film forming liquid that can be degradable or peelable. Mucosal patch 30 may be a solid state film, wherein the film comprises an adhesive layer that dissolves. Mucosal patch 30 may be a sealed liquid film that has a liquid reservoir. The film may have a backing to prevent the acetylcholine from spreading to the application site on soft palate 13, but rather force the acetylcholine to be released to exposed mucosal tissue of the pharyngeal area, e.g., tongue 11 and/or oropharynx 15. The sealed liquid film may deliver the acetylcholine continuously or periodically. In some embodiments, mucosal patch 30 may be removed from patient 10 upon awaking after the sleep period. In other embodiments, mucosal patch 30 may dissolve during the sleep period.

Figure 4:
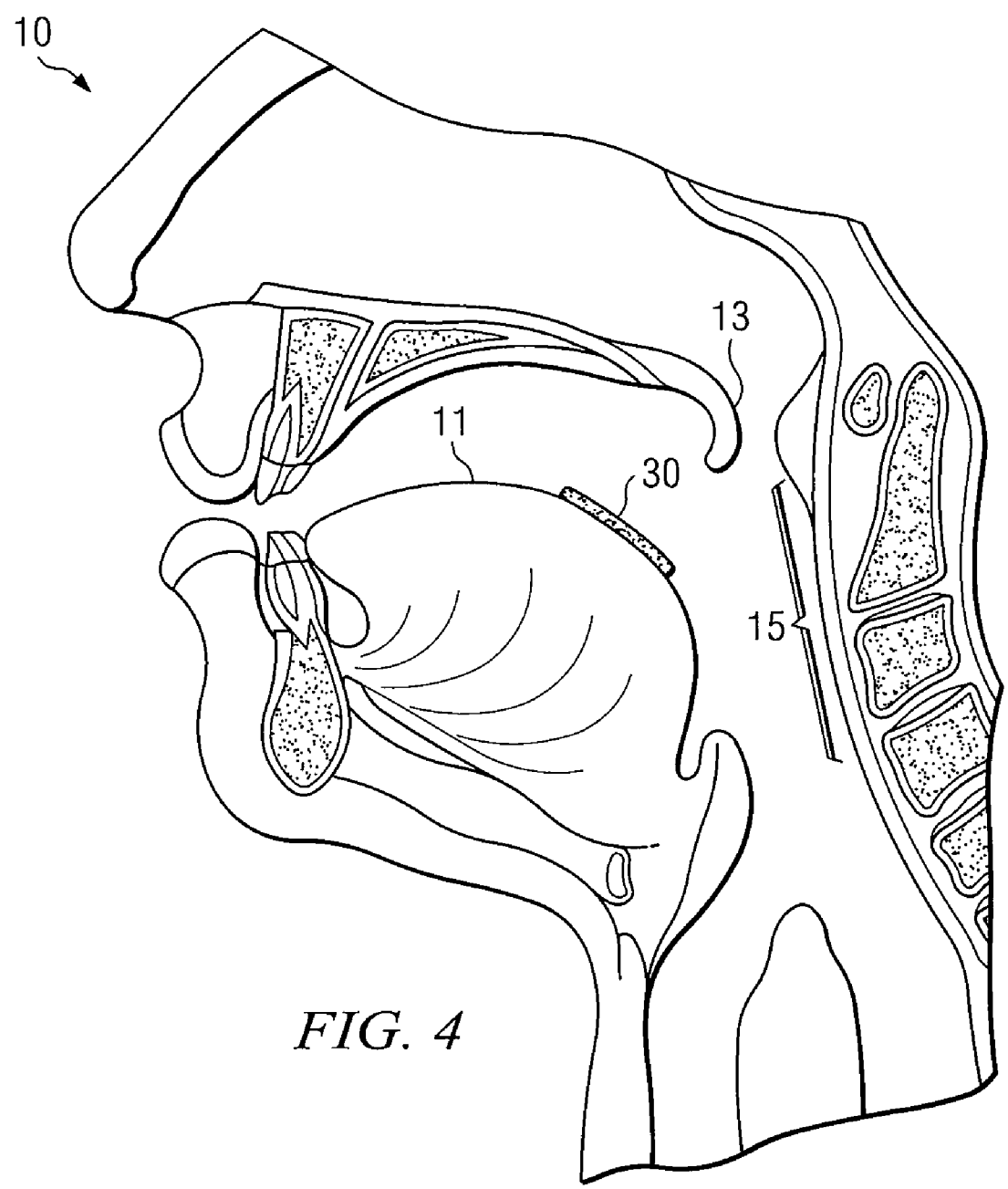
FIG. 4 illustrates another cross-sectional side view of one embodiment of a system for managing at least one breathing condition.

FIG. 4 illustrates a cross-sectional side view of patient 10 and another example system for managing at least one breathing condition, according to one embodiment of the disclosure. In this embodiment, patient 10 may be given a dose of acetylcholine through a mucosal patch delivery system, e.g., prior to patient 10 falling sleep. Mucosal patch 30 may be adhered to tongue 11 in order to deliver acetylcholine to the mucosal tissue of the pharyngeal area, e.g., tongue 11 and/or oropharynx 15. Mucosal patch 30 may be a dissolving film that sticks to oral mucosa. Mucosal patch 30 may be a film forming liquid that can be degradable or peelable. Mucosal patch 30 may be a solid state film, wherein the film comprises an adhesive layer that dissolves. Mucosal patch 30 may be a sealed liquid film that has a liquid reservoir. The film may have a backing to prevent the acetylcholine from spreading to the application site on soft palate 13, but rather forces the acetylcholine to be directed into tongue 11. The sealed liquid film may deliver the acetylcholine continuously or periodically. In some embodiments, mucosal patch 30 may be removed from patient 10 upon awaking after the sleep period. In other embodiments, mucosal patch 30 may dissolve during the sleep period.

Figure 5:
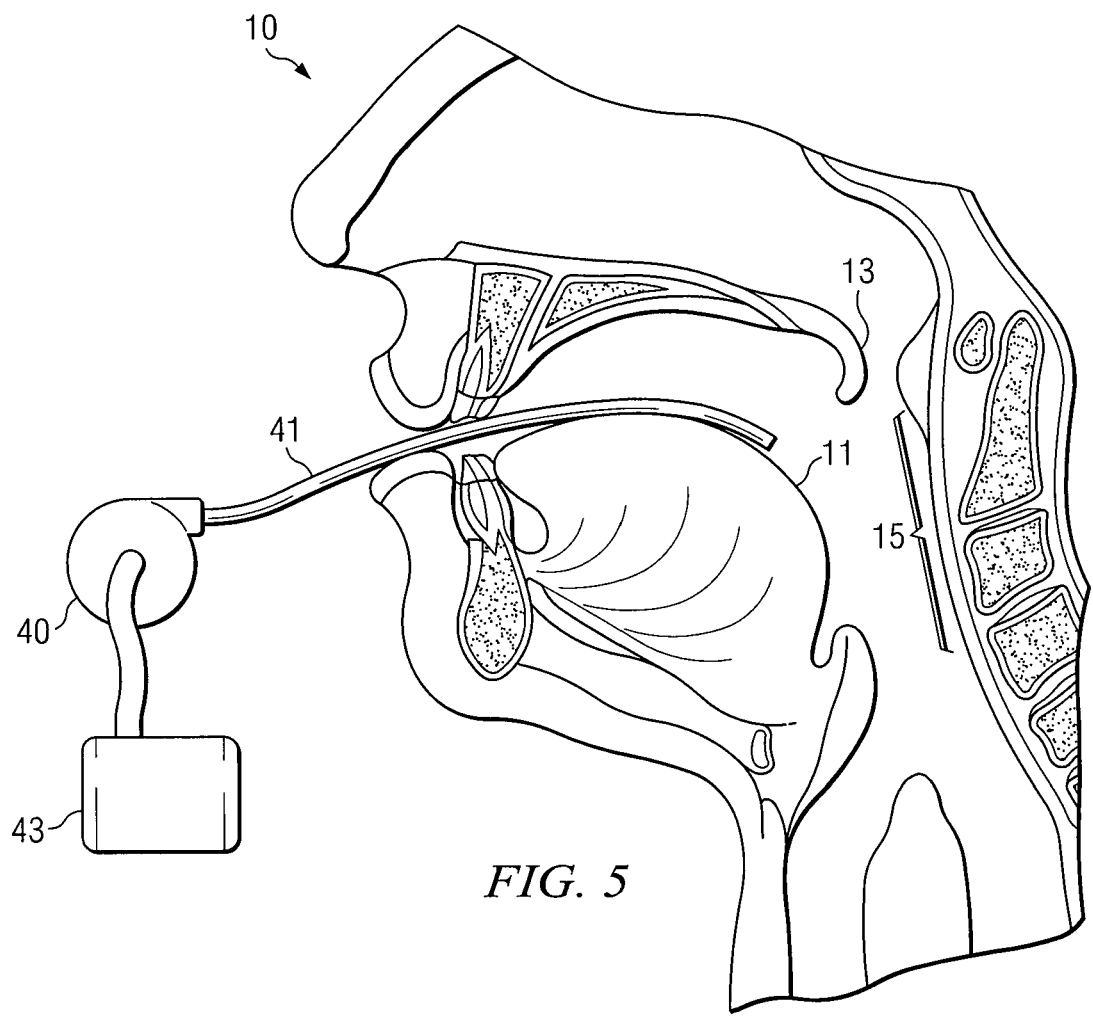
FIG. 5 illustrates another cross-sectional side view of one embodiment of a system for managing at least one breathing condition.

FIG. 5 illustrates a cross-sectional side view of patient 10 and another example system for managing at least one breathing condition, according to one embodiment of the disclosure. In this embodiment, a dose of acetylcholine may be delivered to patient 10 through an external pump delivery system. Pump 40 may be placed near patient 10 and secured in position to prevent inadvertent displacement by patient 10 during the sleep period. Pump 40 may be programmable to adjust the amount, concentration, flow rate, and/or other parameter of the acetylcholine delivery. Pump 40 may be programmable according to intermittent or continuous administration patterns. In some embodiments, pump 40 may contain a supply of acetylcholine sufficient to administer acetylcholine throughout the sleep period. Pump 40 may pass acetylcholine in any suitable form (e.g., liquid or aerosol) through catheter 41 for delivery to the mucosal tissue of the pharyngeal area, e.g., tongue 11 and/or oropharynx 15. In some embodiments, the delivery system may also include a reservoir 43, which may supply to pump 40. Reservoir 43 may be integral to, or separate from, pump 40.

Figure 6:
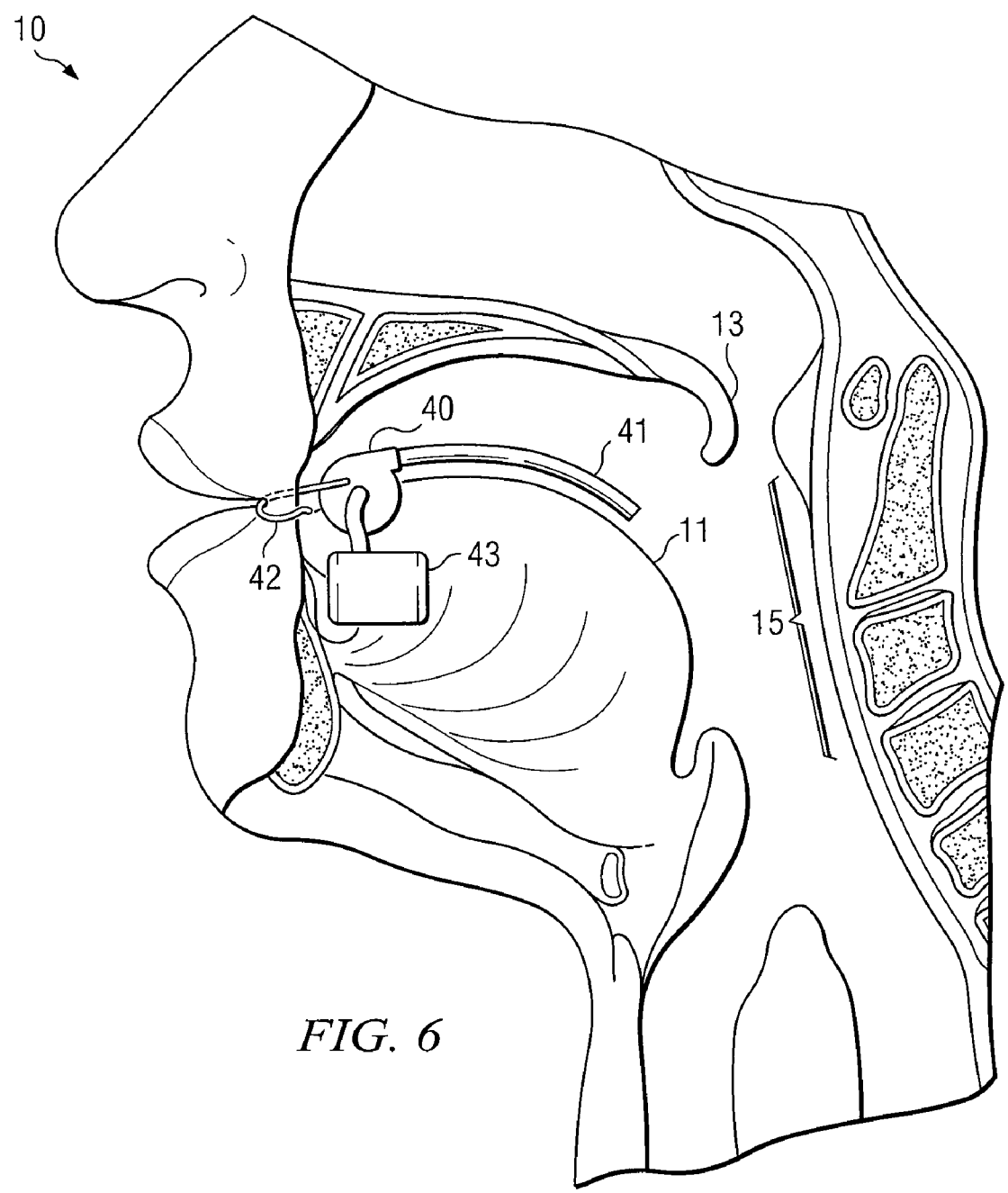
FIG. 6 illustrates another cross-sectional side view of one embodiment of a system for managing at least one breathing condition.

FIG. 6 illustrates a cross-sectional side view of patient 10 and another example system for managing at least one breathing condition, according to one embodiment of the disclosure. In this embodiment, a dose of acetylcholine may be delivered to patient 10 through an internal pump delivery system. Pump 40 may be positioned internally, e.g., in the patient's mouth between the tongue and cheek. In some embodiments, a clip 42 or other securing device may be used to secure pump 40 in a comfortable position inside the patient's mouth. For example, clip 42 may extend from the inside of the patient's cheek, out through the mouth and to the outside of the patient's cheek.

Pump 40 may be programmable to adjust the amount, concentration, flow rate, and/or other parameter of the acetylcholine delivery. Pump 40 may be programmable according to intermittent or continuous administration patterns. In some embodiments, pump 40 may contain a supply of acetylcholine sufficient to administer acetylcholine throughout the sleep period. Pump 40 may pass acetylcholine in any suitable form (e.g., liquid or aerosol) through catheter 41 for delivery to the mucosal tissue of the pharyngeal area, e.g., tongue 11 and/or oropharynx 15. In some embodiments, the delivery system may also include a reservoir 43, which may supply to pump 40. Reservoir 43 may be integral to, or separate from, pump 40.

Pump 40 and/or reservoir 43 may be a replaceable and/or rechargeable unit. For example, in some embodiments, the system may be recharged each day before the system is applied to a patient. In such embodiments, pump 40 and/or reservoir 43 may contain an amount of acetylcholine to treat the patient for one sleep period. Before the system is used again, pump 40 and/or reservoir 43 may be recharged with another dose of acetylcholine to treat the patient for another sleep period.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. A method for managing at least one breathing condition, the method comprising:
   storing an agent in nano-spheres configured to dissolve at different rates, the agent operable to cause increased contraction of muscle tissue in the pharyngeal area and including:
   acetylcholine;
   one or more non-acetylcholine chemicals that slow the rate of degradation of acetylcholine; and
   one or more non-acetylcholine chemicals operable to activate nicotinic receptors to cause the contraction of muscle tissue in the pharyngeal area; and
   depositing the nano-spheres on the mucosal tissue in the pharyngeal area of a patient, the nano-spheres dissolving at different rates such that the agent is delivered to the pharyngeal area in a time-released manner during a sleep period to cause increased contraction of muscle tissue in the pharyngeal area.

2. A method according to claim 1, wherein the agent is operable to provide elevated levels of acetylcholine in muscle tissue in the pharyngeal area.

3. A method according to claim 2, wherein the agent is operable to provide elevated levels of acetylcholine at neuromuscular junctions associated with the muscle tissue in the pharyngeal area.

4. A method according to claim 1, wherein the one or more non-acetylcholine chemicals that slow the rate of degradation of acetylcholine comprises a non-acetylcholine cholinesterase inhibitor.

5. A method according to claim 1, wherein the agent is stored in a mucosal patch positioned on the mucosal tissue of the pharyngeal area, wherein the mucosal patch contains the agent.

6. A method according to claim 1, wherein the agent is stored in a mucosal patch positioned on the mucosal tissue of the soft palate, wherein the mucosal patch contains the agent.

7. A method according to claim 1, wherein the agent is stored in a mucosal patch positioned on the mucosal tissue of the tongue, wherein the mucosal patch contains the agent.

8. A method according to claim 1, wherein delivering the agent comprises pumping the agent to the mucosal tissue of the pharyngeal area.

9. A method according to claim 1, wherein:
the agent is stored in a reservoir associated with a pump; and
delivering the agent comprises pumping the agent through a catheter using the pump.

10. A method according to claim 1, wherein delivering the agent in a time-released manner comprises the dissolving of a mucosal patch.

11. A method according to claim 1, wherein delivering the agent in a time-released manner comprises intermittently pumping the agent during at least a portion of the sleep period.

12. A method according to claim 1, wherein delivering the agent in a time-released manner comprises continuously pumping the agent during at least a portion of the sleep period.

13. A method according to claim 1, wherein the increased contraction of muscle tissue in the pharyngeal area reduces obstructive sleep apnea.

14. A method according to claim 1, wherein the increased contraction of muscle tissue in the pharyngeal area reduces snoring.

15. A system for managing at least one breathing condition, the system comprising:
a volume of nano-spheres containing an agent and operable to deliver the agent to the mucosal tissue in the pharyngeal area, the agent operable to cause increased contraction of muscle tissue in the pharyngeal area and including:
acetylcholine;
one or more non-acetylcholine chemicals that slow the rate of degradation of acetylcholine; and
one or more non-acetylcholine chemicals operable to activate nicotinic receptors to cause the contraction of muscle tissue in the pharyngeal area; and
the volume of nano-spheres including nano-spheres configured to dissolve at different rates, thereby providing a time-release mechanism operable to control the delivery of the agent to the mucosal tissue in the pharyngeal area during a sleep period to cause increased contraction of muscle tissue in the pharyngeal area during the sleep period.

16. A system according to claim 15, wherein the agent is operable to provide elevated levels of acetylcholine in muscle tissue in the pharyngeal area.

17. A system according to claim 16, wherein the agent is operable to provide elevated levels of acetylcholine at neuromuscular junctions associated with the muscle tissue in the pharyngeal area.

18. A system according to claim 15, wherein the one or more non-acetylcholine chemicals that slow the rate of degradation of acetylcholine comprises a non-acetylcholine cholinesterase inhibitor.

19. A system according to claim 15, wherein, in addition to acetylcholine, the agent further comprises one or more non-acetylcholine chemicals operable to activate nicotinic receptors to cause the contraction of muscle tissue in the pharyngeal area.

20. A system according to claim 15, wherein the agent delivery device comprises a mucosal patch.

21. A system according to claim 15, wherein the agent delivery device comprises a pump.

22. A system according to claim 15, wherein the time-release mechanism comprises a mucosal patch that dissolves during the sleep period.

23. A system according to claim 15, wherein the time-release mechanism comprises a pump that operates during at least portions of the sleep period.

24. A system according to claim 15, wherein the increased contraction of muscle tissue in the pharyngeal area reduces obstructive sleep apnea.

25. A system according to claim 15, wherein the increased contraction of muscle tissue in the pharyngeal area reduces snoring.

\* \* \* \* \*